US011311421B2

(12) United States Patent
Lipshaw et al.

(10) Patent No.: US 11,311,421 B2
(45) Date of Patent: Apr. 26, 2022

(54) REDUCTION KITS

(71) Applicant: MEDI MANUFACTURING, INC., Whitsett, NC (US)

(72) Inventors: Moses A. Lipshaw, Encinitas, CA (US); Teresa Kennerknecht, Culver City, CA (US); Thomas Richardson, San Diego, CA (US); Sandra Anne Shaw, Port S. Lucie, FL (US); Dean J. Bender, Terrell, NC (US)

(73) Assignee: MEDI MANUFACTURING, INC., Whitsett, NC (US)

( * ) Notice: Subject to any disclaimer, the term of this patent is extended or adjusted under 35 U.S.C. 154(b) by 950 days.

(21) Appl. No.: 14/836,653

(22) Filed: Aug. 26, 2015

(65) Prior Publication Data
US 2016/0058623 A1 Mar. 3, 2016

Related U.S. Application Data

(60) Provisional application No. 62/044,921, filed on Sep. 2, 2014.

(51) Int. Cl.
*A61F 13/06* (2006.01)
*A61F 13/08* (2006.01)
*A61F 13/10* (2006.01)

(52) U.S. Cl.
CPC .......... *A61F 13/06* (2013.01); *A61F 13/064* (2013.01); *A61F 13/085* (2013.01); *A61F 13/102* (2013.01); *A61F 13/108* (2013.01)

(58) Field of Classification Search
CPC .......... A61F 13/00021; A61F 13/00038; A61F 13/00029; A61F 13/085; A61F 13/062; A61F 13/06; A61F 13/064; A61F 13/102; A61F 13/108; A61F 13/00; A61F 13/10; A61F 13/08; A61F 13/061; A61F 13/107; A61F 5/01; A61F 5/0118; A61F 5/013; A61F 5/058; A61F 5/05841; A61F 5/05858; A61F 5/0585; A61F 5/0123; A61F 5/0102; A61F 5/0111; A61F 2013/00093
USPC .... 602/60, 75, 19, 23, 26, 61–63, 5, 20, 21, 602/27, 41, 64–65; 606/201; 128/878, 128/881, 882
See application file for complete search history.

(56) References Cited

U.S. PATENT DOCUMENTS

| 3,945,046 | A | * | 3/1976 | Stromgren | A61F 13/062 |
| | | | | | 602/63 |
| 5,918,602 | A | | 7/1999 | Shaw et al. | |
| 6,254,554 | B1 | | 7/2001 | Turtzo | |
| 7,556,608 | B2 | * | 7/2009 | Parizot | A61F 5/028 |
| | | | | | 128/96.1 |
| 2006/0122547 | A1 | * | 6/2006 | Stewart, III | A61F 5/028 |
| | | | | | 602/19 |
| 2007/0179421 | A1 | * | 8/2007 | Farrow | A61H 9/005 |
| | | | | | 602/75 |

(Continued)

FOREIGN PATENT DOCUMENTS

WO 2010025186 A1 3/2010
WO 2015009747 A2 1/2015

*Primary Examiner* — Caitlin A Carreiro
(74) *Attorney, Agent, or Firm* — Rimôn, P.C.

(57) ABSTRACT

Customizable garments and kits, including uses thereof, having adaptations for ease of positioning for providing therapeutic compression such as compression therapy for the treatment of circulatory disorders such as Lymphedema and Venous Disease.

16 Claims, 4 Drawing Sheets

(56) References Cited

U.S. PATENT DOCUMENTS

| | | | |
|---|---|---|---|
| 2010/0312160 A1* | 12/2010 | Creighton | A61L 15/42 602/62 |
| 2012/0179084 A1 | 7/2012 | Lipshaw et al. | |
| 2013/0072837 A1 | 3/2013 | Rousso et al. | |
| 2015/0025424 A1* | 1/2015 | Richardson | A61F 13/085 601/84 |

* cited by examiner

REDUCTION KITS

CROSS-REFERENCE TO RELATED APPLICATIONS

This application claims priority to U.S. Provisional Patent Application No. 62/044,921, filed Sep. 2, 2014, which incorporated herein by reference in its entirety.

TECHNICAL FIELD

The present invention relates to compression therapy garments and kits, including their use.

BACKGROUND

Lymphedema is swelling that occurs when excessive protein-rich lymph fluid accumulates in the interstitial tissue. This lymph fluid may contain plasma proteins, extravascular blood cells, excess water, and parenchymal products. Lymphedema is one of the most poorly understood, relatively underestimated, and least researched complications of common diseases like cancer, and thus the prevalence of lymphedema within the general population is largely unknown. Nevertheless, for those who are diagnosed with lymphedema, the standard of care consists of meticulous skin care, manual lymphatic drainage, exercise therapy, inelastic compression bandaging and, eventually, compression garments.

The frequency and duration of care is dependent on individual subject's therapeutic need and may range from 2 to 3 visits per week for 6 or more weeks depending on the severity of lymphedema and any other associated impairment.

The use of compression bandaging, although proven effective in reducing edema, has its drawbacks. The application of inelastic compression bandages is time consuming and requires a skilled clinician. Furthermore, because subjects are not able to effectively bandage themselves, this treatment strategy does not promote self-care, does not provide sustained therapeutic levels of compression, and requires the subject to frequently return for follow up visits. Lastly, wearing bandages negatively impacts the subject's quality of life with regard to comfort and hygiene which can reduce compliance.

Many bandage alternative wrap type garments exist on the market. These garments are primarily used after the intensive phase treatment of lymphedema to maintain the patient's limb size. Most of the wrap garments lack the ability to adapt to changes in limb size and are cost prohibitive to be used as a short term bandage replacement in the intensive phase. For those garments that are available the sizing adjustments can be complex and time consuming for practical use.

The embodiments of the present disclosure address these and other related needs in the art.

SUMMARY

In certain embodiments a compression garment is provided, comprising: a body dimensioned to wrap at least partially around a length of a limb of a subject, wherein the body has an adjustable length; a plurality of trimmable tension bands positioned along the adjustable length of the body; a limb positioning sleeve positioned on the body and/or tension bands; and a plurality of removable fasteners for attachment onto the body or tension bands. The limb positioning sleeve can be a guide sleeve.

In frequent embodiments each of the plurality of fasteners comprises a hook and/or loop fastener. In other embodiments, one or more of the fasteners comprises a hook and loop fastener. Frequently, the fastener comprises a hook fastener. Often, a number of the plurality of removable fasteners corresponds to a number of the plurality of trimmable tension bands. Also, often each of the plurality of removable fasteners attaches an extension band onto the body or one of the plurality of trimmable tension bands.

In certain embodiments the body and the trimmable tension bands are comprised of a single contiguous piece of material or laminate. Often, the contiguous piece of material is permeable to fluids.

In frequent embodiments, a number or each of the tension bands comprises measurement indicia that provides an indication of tension in or displacement of the corresponding tension band.

Often, the compression garment is customizable to be sized to fit a subject by adjusting the adjustable length of the body and/or trimming any of the trimmable tension bands to remove excess material when wrapped around the limb of the subject.

In certain frequent embodiments, the limb positioning sleeve comprises a flap having a first end affixed to the body or the tension band, and a second end that is removably attachable onto the flap, the body, the tension band, or a second flap affixed to the body or the tension band. Often, the limb positioning sleeve comprises a first flap and a second flap, wherein the first and second flap are removably attached or attachable onto one-another. Also often, the limb positioning sleeve comprises a first flap and a second flap, each flap having a respective first end affixed to the body or the tension band, wherein the first and second flap are removably attached or attachable to one-another.

Frequently, the compression garment comprises an adjustable length of the body that is adjusted by removing a portion of the adjustable length of the body. Often, a portion of a trimmable tension band, or an entire trimmable tension band, is removed by adjusting the length of the body. Guide indicia are often provided to show where the body or bands should be cut. Also, the adjustable length of the body is often adjusted by removing a portion of the adjustable length of the body and at least a portion of one or more of the plurality of trimmable tension bands. Also frequently, the adjustable length of the body is adjusted by removing a portion of the adjustable length of the body and one or more of the plurality of trimmable tension bands.

In frequent embodiments, one or more of the plurality of trimmable tension bands is trimmed to remove a portion of a length of the trimmable band to produce a plurality of trimmed bands when or after it is wrapped around the limb of a subject. Often, each of the removable fasteners is attached to an associated/respective end of each of the trimmable tension bands. In certain frequent embodiments, at least about 75% of the plurality of trimmable tension bands have the same width. Often, at least about 85% of the plurality of trimmable tension bands have the same width.

Each of the plurality of trimmable tension bands most frequently comprises a solid contiguous material or laminate. Often, at least one of the plurality of trimmable tension bands comprises multiple materials having differing material properties.

In certain embodiments, the body comprises two or more detachable pieces. In such embodiments, often the two or more detachable pieces are positionable at positions onto each piece opposed to a respective position of the trimmable tension bands.

Frequently, the compression garment comprises an arm wrap reduction kit or a leg wrap reduction kit. Often, the compression garment comprises a foot or hand wrap reduction kit.

Methods of using the reduction kits of the present disclosure. Often a method of using the compression of garment of the present disclosure is provided, comprising positioning a limb of a subject in the limb positioning sleeve, applying tension to each of the plurality of trimmable tension bands to provide a predetermined level of compression to the limb, and attaching a removable fastener to each of the plurality of trimmable tension bands to fasten the band at the predetermined level of compression. Frequently, the method further comprises removing a portion of one or more of the plurality of trimmable tension bands. Often, the pre-determined level of compression is obtained using an assured tension measuring system. Also, frequently, the subject performs each step of the claimed method without the aid of a clinician or another person.

Methods are also provided, similar to the above, whereby the subject continues to remove portions of one or more of the plurality of trimmable tension bands over time as a level of lymphedema decreases in the subject.

Methods of manufacturing the garments described herein (e.g., a foot wrap, a hand wrap, an arm wrap, a leg wrap, etc.) are also contemplated such that a compression garment is manufactured comprising a single contiguous piece of material such as fabric having a known or predetermined elasticity profile. These garments are manufactured to be specifically fitted to a specific limb of a subject. Such garments are often trimmable garments, optionally including one or more removable fasteners, as further described herein.

DETAILED DESCRIPTION

Figure 1:
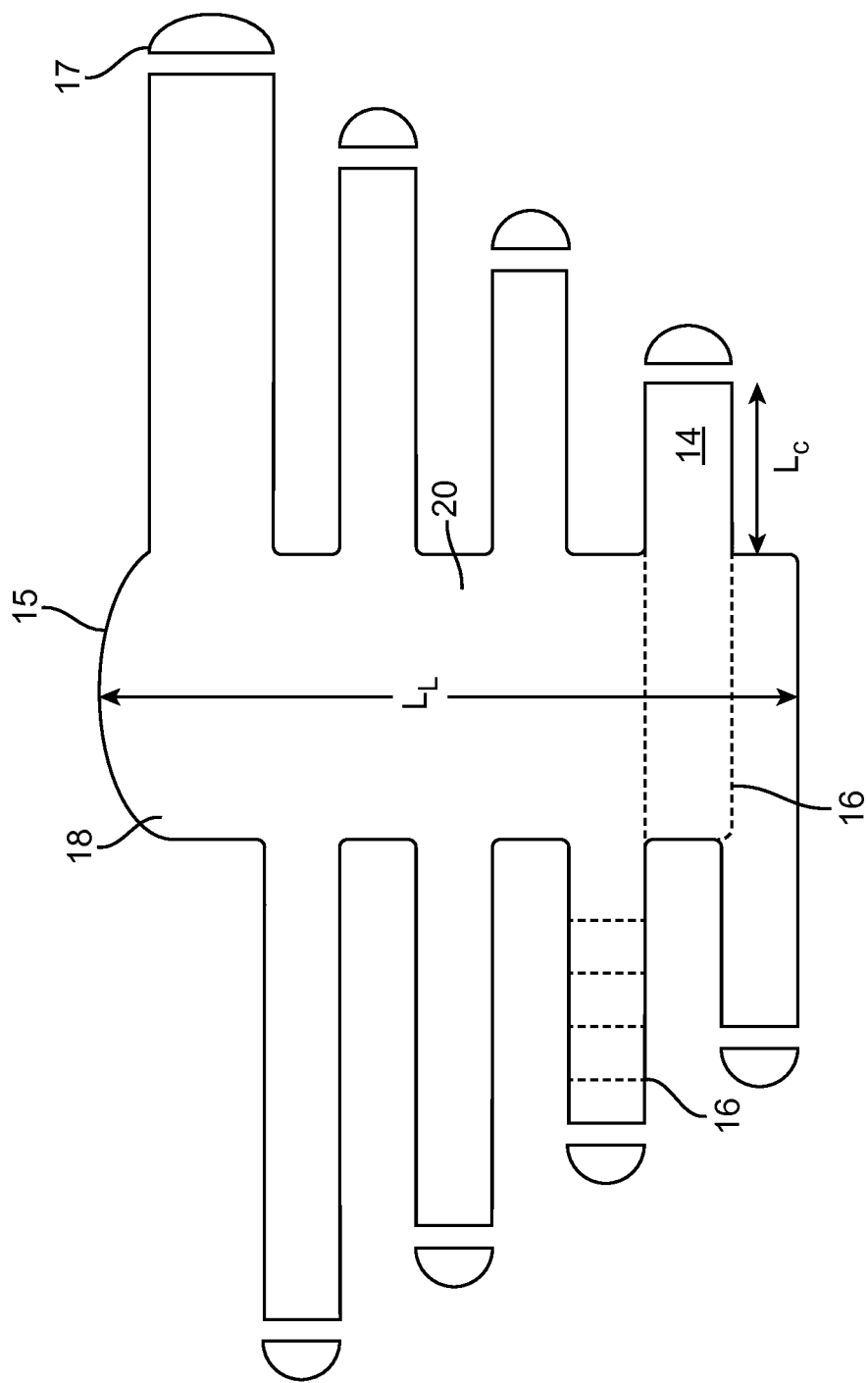
FIG. 1 depicts one exemplary embodiment of an arm wrap of the present disclosure.

Unless defined otherwise, all terms of art, notations and other scientific terms or terminology used herein have the same meaning as is commonly understood by one of ordinary skill in the art to which this invention belongs. In some cases, terms with commonly understood meanings are defined herein for clarity and/or for ready reference, and the inclusion of such definitions herein should not necessarily be construed to represent a substantial difference over what is generally understood in the art. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "subject" is not limited to a specific species. For example, the term "subject" may refer to a patient, and frequently a human patient. However, this term is not limited to humans and thus encompasses a variety of mammalian species.

As used herein, "reduction kit" refers to any of a variety of single or contiguous material, one-size-fits-all compression modules or garments specific to a specific limb or portion thereof, or other part of a subject's body, comprised of inelastic material that is easily adjustable.

In certain embodiments a reduction kit of the present disclosure comprises a one-size-fits-all, easy-to-use, inelastic, instantly adjustable compression bandage module that is fitted to a subject's limb in a medical clinic and/or by a medical professional. In the most frequent embodiments, reduction kits of the present disclosure comprise a single contiguous piece of material designed, cut, and adapted to fit and provide therapeutic compression to a particular part or region of a subject. The term "contiguous" is used herein to refer to a single material or co-extensive laminate of materials. Materials that are comprised of partially overlapping and non-coextensive layers, or are comprised of materials/sheets that are attached end-to-end are not considered to be a single contiguous material as that term is used herein.

Such kits need only be trimmed and attached using fasteners to provide a customized fit to all subjects. In particularly frequent embodiments, the kits also include a guide sleeve as further described below and depicted herein.

These reduction kits often comprise upper or lower extremity wraps and are made of breathable material that has sufficient elasticity to follow the contour of the limb and thickness to bridge skin folds, maximizing comfort and reducing slippage. Certain exemplary materials include, for example, BREATH-O-PRENE® material (available from Accu-Med Technologies, Inc., Buffalo, N.Y.). Such materials have surfaces that are often useable with hook fasteners that attach directly to the garment, without the use of a specific loop material to work in conjunction with the hook fastener.

In certain embodiments, a reduction kit of the present disclosure comprises a body and a series of juxtaposed bands that are wrapped around the limb and fastened with hook and loop closures, which allows for quick and easy application, as well as removal and adjustment of the garment. Once first applied by the clinician or the like, a subject can often therafter easily and quickly apply the reduction kit consistently at a pre-determined compression level (which can be adjusted) without assistance from a clinician. This ease of use increases compliance and hygiene, which greatly improves the therapeutic effect of the use of the reduction kit with far fewer follow-up sessions. In certain frequent embodiments, the reduction kit also features an assured tension measuring system, which ensures the patient can sustain the same compression as applied by the clinician. See, for example, U.S. Pat. Nos. 6,338,723 and 7,329,232, each of which is incorporated herein by reference.

The quick, simple and therapeutic application of the reduction kit combines to give the subject a comfortable, clean and effective system that will not unduly hinder their lifestyle or state of mind while effectively delivering therapeutic compression and, for example, managing edema.

Arm Wrap

In certain embodiments, an arm wrap reduction kit is provided having a body I as a flat piece of fabric with a series of juxtaposed bands 14 designed to cover the arm of a subject from the subject's wrist to the axilla. The bands 14 are designed to be wrapped around the arm and tightened to provide compression and are attached to the body 20 or back unto themselves with, for example, hook and loop fastener tabs, e.g., hook tabs 17. The hook tabs 17 are often kept separate, or are otherwise positioned on the kit or unattached to the kit while sizing so the length $L_C$ of the band, e.g., band 14, can be trimmed to the length that best fits the limb of the specific subject. Frequently, the length $L_C$ is longer than the width of the body 20 portion in that region so that a larger range of limb circumferences can be accommodated. Additionally, in certain embodiments, a portion of the body 20 and one or more bands 14 may be removed from the garment to reduce the overall length $L_L$ in order to fit the limbs of certain subjects. In frequent embodiments, indicia or cut marks 16 are present on the garment to guide the trimming and fitting of the kit to the correct size. Indicia or cut marks 16 refer to an indication on the kit to guide removal of portions of the body 18, portions of bands and/or entire bands 14.

In frequent embodiments, the arm wrap reduction kit also includes a lateral rise 15 that is provided to apply compression to the subject by the reduction kit beyond the end of the sleeve or body 18 further up the limb, for example, laterally beyond an outermost band 14 to reach additional areas of the subject such as past the axilla onto the shoulder. In leg garment versions, this lateral rise 15 coverage area optionally extends above the groin onto the thigh.

Figure 2:
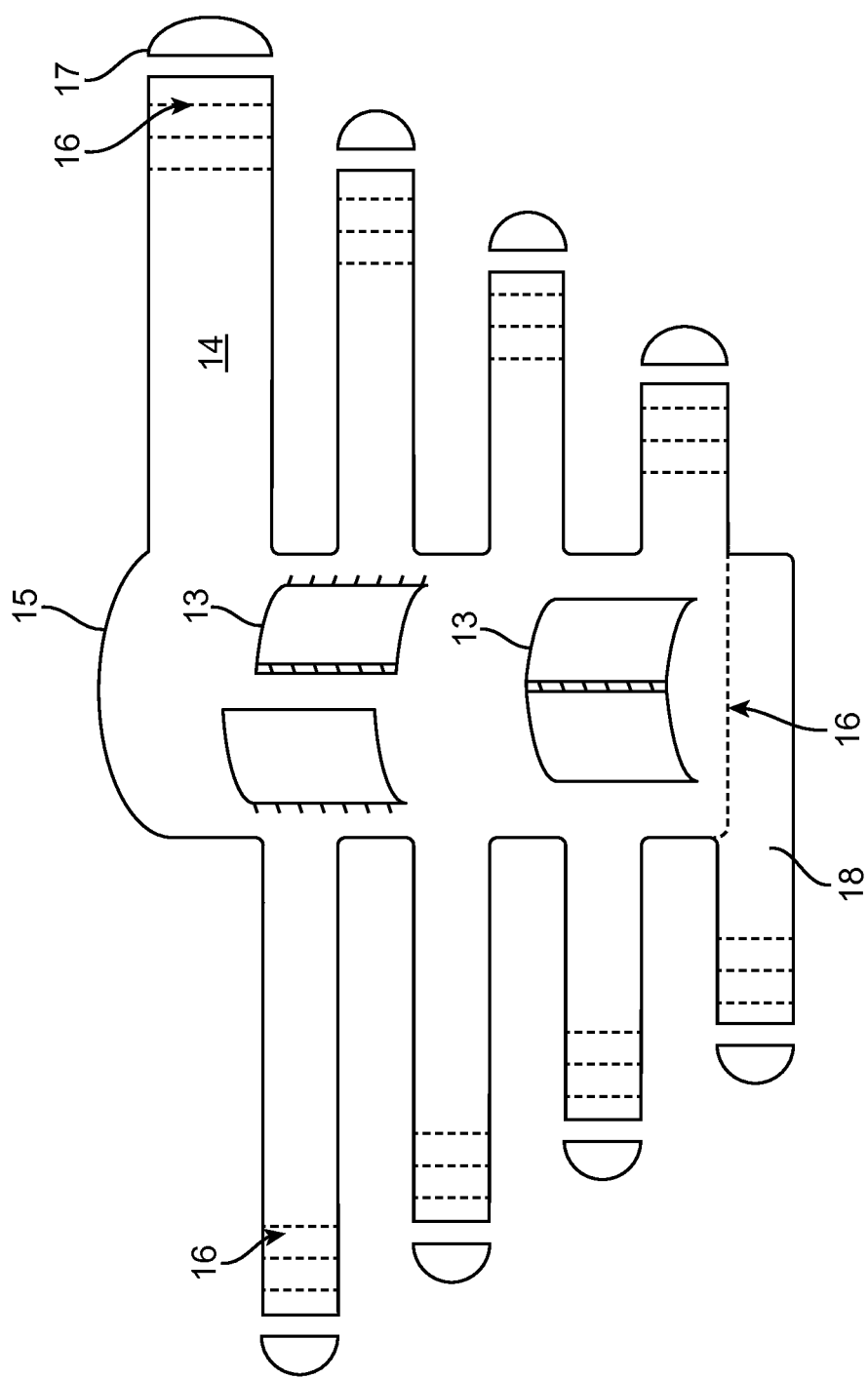
FIG. 2 depicts another exemplary embodiment of an arm wrap of the present disclosure.

Given that the user only has one arm available to tighten and apply the bands, it is often beneficial to incorporate a guide sleeve, for example two or more guide sleeves 13 in FIG. 2 to hold the body 18 and bands 14 in position on the limb of the subject prior to tightening and/or while being tightened. Guide sleeves are often beneficial on arm wrap embodiments of the present disclosure, but may be provided on other embodiments such as leg, foot, hand wraps, or the like. In various embodiments, there may be one or more of these sleeves as needed on the reduction kit.

Frequently the disclosed guide sleeves are trimmable or trimmed to a length that optimizes their fit on a specific subject. In frequent embodiments, these sleeves are secured with fastener tabs (e.g., hook and/or loop tabs). FIG. 2 depicts two guide sleeves 13, one in a closed orientation, and the other (closer to the lateral rise) in an open orientation. As can be seen in the open orientation, the guide sleeve may comprise two flaps, either or both of which can be trimmed to a shorter length and the two ends can be removably attached with a fastener tab.

In certain embodiments, one of the flaps of the guide sleeve 13 is not trimmable and comprises an attached fastener (e.g., a hook and/or loop fastener), to fasten it to the other flap, which may be trimmable. The opposite ends of the flaps that are not trimmed or trimmable are often attached in a permanent, semi-permanent, or removable manner to the body of the reduction kit.

Although exemplary guide sleeves depicted herein are provided in a dual flap arrangement, other embodiments of guide sleeves useable with the present reduction kits include, for example, a tube attached or attachable to the body of the garment that the subject may use by sliding the tube over a specific limb. A variety of other configurations and orientations are contemplated.

Figure 3:
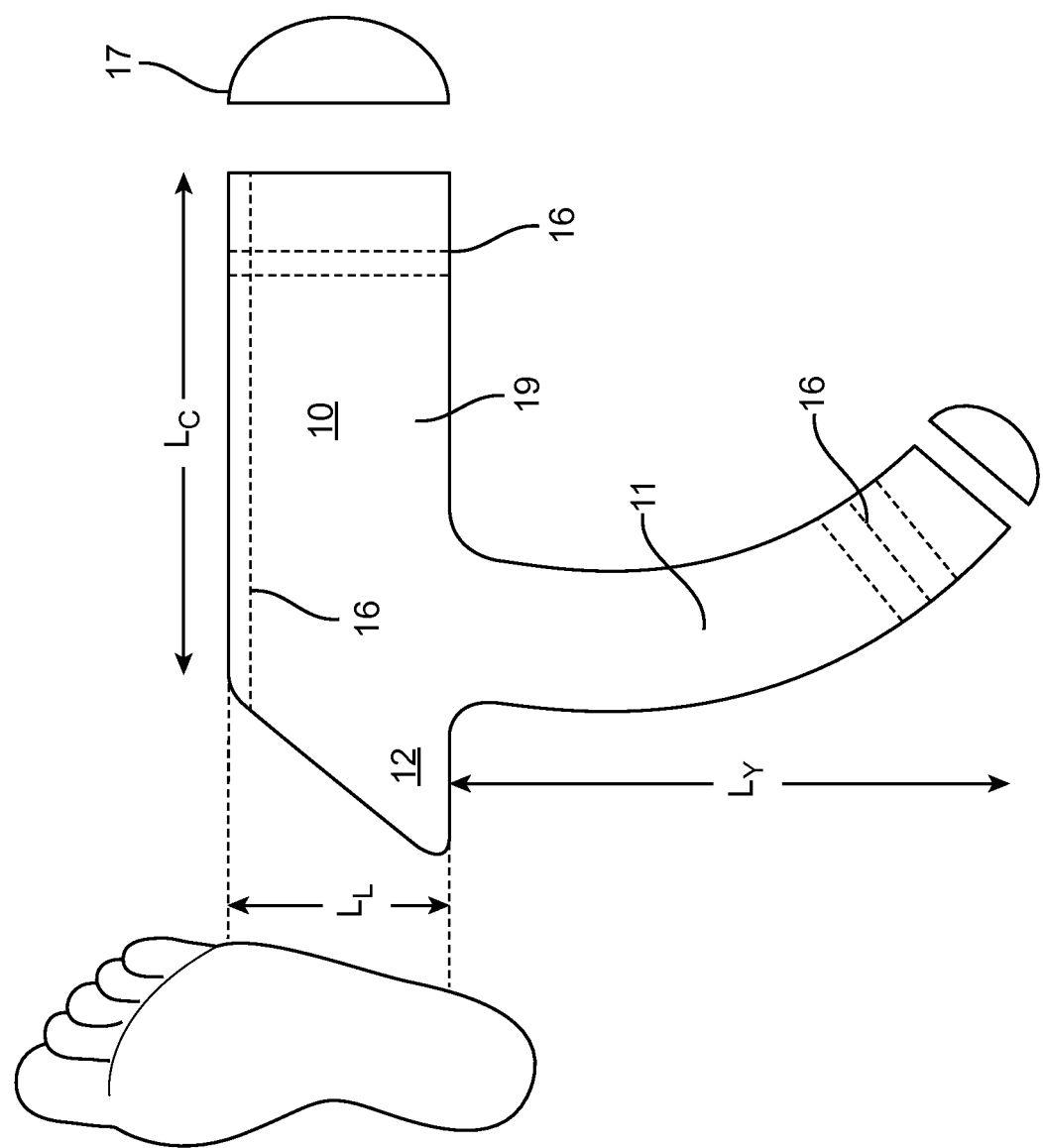
FIG. 3 depicts one exemplary embodiment of a foot wrap of the present disclosure positioned adjacent to a foot for illustrative purposes.
Figure 4:
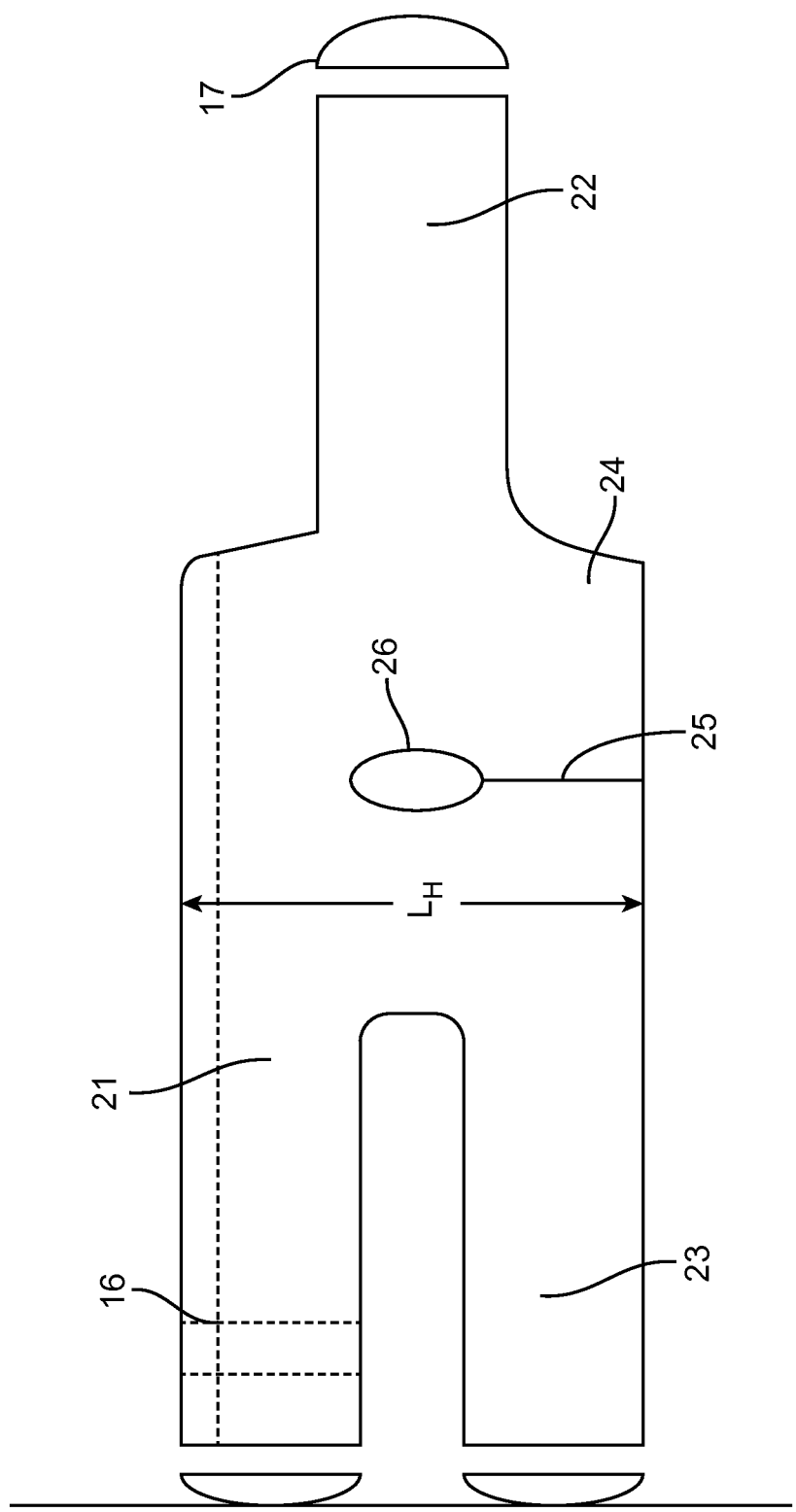
FIG. 4 depicts one exemplary embodiment of a hand wrap of the present disclosure.

Foot Wrap:

An exemplary embodiment of a foot wrap reduction kit is depicted in FIG. 3. This foot wrap includes, for example, trim indicia or markings 16 to guide the user to the proper fit. Though not wishing to be bound by theory, the wrap is intended to cover and apply compression to key areas of the foot such as the arch and below the malleoli. Additional compression to other areas of the foot is often applied via a compression anklet, compression stocking, or another garment or device.

In certain embodiment, to apply the foot wrap, tab 12 is held by a subject or clinician in one hand while the arch band 10 is wrapped around the arch of the foot and secured back unto itself with separate Velcro hook tab 17. The heel band 11 is then wrapped over the malleoli behind the foot around the achilles and attached onto the arch band 11. The foot length fit $L_L$ can be adjusted by trimming the arch band, for example, along dotted line 16. The arch circumference $L_C$ fit can be adjusted, for example, by trimming the length of the arch band 10, for example, along dotted line 16. The placement of the arch band 10 towards or away from the toes can be adjusted, for example, by trimming the heel band 11 length $L_Y$, for example, along dotted line 16.

Hand Wrap:

Frequent embodiments of the hand wrap reduction kit 24 are intended to cover the hand of a subject, from near the base of the fingers to the wrist. The hand wrap consists of a series of juxtaposed bands similar to the arm wrap 18, but also including a thumb hole 26 to anchor the wrap in place on the subject's thumb. In use of such embodiments, the palm and fingers of the subject can be covered, for example, by wrapping band 21 around the hand and attaching it back onto itself via hook tab 17. Band 22 can be similarly applied and covers, for example, the back of the hand starting at the thumb. Band 23, in frequent embodiments, continues to cover the wrist area and may be shorter or extended longer to cover further up the subject's arm in a bandaging fashion. The garment may include a dart 25 or multiple darts to better conform to the curvature of the subject's limb. In the most frequent embodiments, indicia and markings 16 are present to aid in guiding trimming and sizing of the hand wrap. The bands can be trimmed, for example, to be sized to smaller circumferences. In addition, in certain embodiments the wrap length $L_H$ can be shortened to cover more or less of the hand and fingers.

With regard to each of the embodiments described here, most frequently each is comprised of a single contiguous piece of material (e.g., fabric), often with a known or pre-determined elasticity profile. The single piece of material garment is often provided with indicators for tension application (e.g., compression indicators) on a specific portion of the limb (e.g., different levels of compression may be applied to a single limb) or on the limb overall. Often, a guide sleeve is included or formed on the garment to aid in accurate placement of the garment on a limb without the need for assistance of another person or health care professional. Moreover, most frequently, the single contiguous piece of material is adapted to be trimmed to remove portions of the material that aid in fitting a single size of the garment to a subject, regardless of the specific size of the limb of the subject. Most frequently, the body and/or a band may be trimmed to remove material, for example as depicted and explained herein. As is known in the art, limb size varies between subjects. Also, as therapy progresses for a specific subject, their limb size often changes such as getting smaller for example due to decreased lymphedema induced limb swelling. There are a variety of advantages that have been discovered by the inventors as part of this innovation as noted herein, as well as for ease in manufacturing of garments in a single size that fits different subjects having different sized limbs. Less occasionally, 2 or 3 sizes are provided that are adjustable or trimmable to fit a full range of limb sizes. Removable tabs are often provided to aid in accurate placement of the garment before or after trimming.

Other features and advantages of the invention will be apparent from the description herein. The examples are provided herein are solely to illustrate the invention by reference to specific embodiments. These exemplifications, while illustrating certain specific aspects of the invention, do not portray the limitations or circumscribe the scope of the disclosed invention. Many variations to those described above are possible.

We claim:

1. A compression garment, comprising:
a body dimensioned to wrap at least partially around a limb of a subject, wherein the body has a length that is adjustable;
a plurality of trimmable tension bands, extending from the body in a direction that is perpendicular to the length of the body, each band of the plurality of trimmable tension bands having a band width and a band length, wherein the band length is adjusted by trimming the band; wherein the plurality of trimmable tension bands are configured to be wrapped around the limb of the subject and tightened to provide compression to the limb; and wherein a portion of the body and one or more of the plurality of trimmable tension bands are removed to reduce an overall length of the garment;
an adjustable limb positioning sleeve configured to hold the body and the plurality of trimmable tension bands on the limb of the subject prior to or during tightening, the adjustable limb positioning sleeve comprising a first flap and a second flap, each having a respective first end affixed to the body at an attachment position, and each having a respective second end that is configured to be trimmed to a shorter length to optimize fit on the limb of the subject, wherein the second end of the first flap is removably attachable to the second end of the second flap, wherein the first and second flaps are each dimensioned to have a sleeve width that is smaller than the length of the body at least at the attachment position, and wherein the sleeve width is smaller than the band width of each of the plurality of trimmable tension bands; and
a plurality of fastener tabs that are each configured to be attached to an associated end of each of the plurality of trimmable tension bands after the band length of each band is adjusted by trimming the band, wherein the plurality of fastener tabs are adapted to provide attachment of each of the plurality of trimmable tension bands onto the body or onto one or more of the plurality of trimmable tension bands when each of the plurality of trimmable tension bands is wrapped around the limb of the subject and tightened to provide compression to the limb.

2. The compression garment of claim 1, wherein the body comprises two or more detachable pieces.

3. The compression garment of claim 2, wherein the two or more detachable pieces are positionable at positions onto each piece opposed to a respective position of the plurality of trimmable tension bands.

4. The compression garment of claim 1, wherein the body and the plurality of trimmable tension bands are comprised of a single contiguous piece of material or laminate.

5. The compression garment of claim 1, wherein a number of the plurality of trimmable tension bands comprises a measurement indicia that provides an indication of tension in or displacement of each of the plurality of trimmable tension bands having the measurement indicia.

6. The compression garment of claim 1, wherein the compression garment is configured to be sized to fit the limb of the subject by adjusting the length of the body and/or by trimming any of the plurality of trimmable tension bands to remove excess material when wrapped around the limb of the subject.

7. The compression garment of claim 1, wherein the length of the body is adjusted by removing a portion of the body.

8. The compression garment of claim 1, wherein the band width of one or more of the plurality of trimmable tension bands is different than the band width of one or more remaining bands of the plurality of trimmable tension bands, and at least about 75% of the plurality of trimmable tension bands are dimensioned to have a similar band width.

9. The compression garment of claim 1, wherein at least one of the plurality of trimmable tension bands comprises multiple materials having differing material properties.

10. A method of using the compression garment of claim 1, comprising
positioning a limb of a subject in the adjustable limb positioning sleeve,
applying tension to each of the plurality of trimmable tension bands to provide a predetermined level of compression to the limb, and
attaching one of the plurality of fastener tabs to each of the plurality of trimmable tension bands to fasten each of the plurality of trimmable tension bands at the predetermined level of compression.

11. The method of claim 10, further comprising removing a portion of one or more of the plurality of trimmable tension bands.

12. The method of claim 10, wherein the pre-determined level of compression is obtained using an assured tension measuring system.

13. The method of claim 10, wherein the subject performs each step of the claimed method without the aid of a clinician or another person.

14. The method of claim 10, wherein the subject continues to remove portions of one or more of the plurality of trimmable tension bands over time as a level of lymphedema decreases in the subject.

15. A method of using the compression garment of claim 1, comprising
positioning a limb of a subject in the adjustable limb positioning sleeve, and
applying tension to each of the plurality of trimmable tension bands to provide a predetermined level of compression to the limb.

16. A compression garment, comprising:
a body dimensioned to wrap at least partially around a limb of a subject, wherein the body has a length that is adjustable;
a plurality of trimmable tension bands extending from the body in a direction that is perpendicular to the length of the body, each band of the plurality of trimmable tension bands having a band width and a band length, wherein the band length is adjusted by trimming the band, and wherein the band width of one or more of the plurality of trimmable tension bands is different than the band width of one or more remaining bands of the plurality of trimmable tension bands and at least about 75% of the plurality of trimmable tension bands are dimensioned to have a similar band width; wherein the plurality of trimmable tension bands are configured to be wrapped around the limb of the subject and tightened to provide compression to the limb; and wherein a portion of the body and one or more of the plurality of trimmable tension bands are removed to reduce an overall length of the garment;

an adjustable limb positioning sleeve configured to hold the body and the plurality of trimmable tension bands on the limb of the subject prior to or during tightening, the adjustable limb positioning sleeve comprising a first flap and a second flap, each having a respective first end affixed to the body at an attachment position, and each having a respective second end that is configured to be trimmed to a shorter length to optimize fit on the limb of the subject, wherein the second end of the first flap is removably attachable to the second end of the second flap, wherein the first and second flaps are each dimensioned to have a sleeve width that is smaller than the length of the body at the attachment position, and wherein the sleeve width is smaller than the band width of each of the plurality of trimmable tension bands; and a plurality of fastener tabs that are each configured to be attached to an associated end of each of the plurality of trimmable tension bands after the band length of each band is adjusted by trimming the band, wherein the plurality of fastener tabs are adapted to provide attachment of each of the plurality of trimmable tension bands onto the body or onto one or more of the plurality of trimmable tension bands when each of the plurality of trimmable tension bands is wrapped around the limb of the subject and tightened to provide compression to the limb.

* * * * *